United States Patent [19]

Siegel et al.

[11] Patent Number: 5,225,595

[45] Date of Patent: Jul. 6, 1993

[54] ARYLSULFONYL COMPOUNDS WITH UNSATURATED RADICALS

[75] Inventors: Bernd Siegel, Ludwigshafen; Claus Marschner, Speyer; Manfred Patsch, Wachenheim, all of Fed. Rep. of Germany

[73] Assignee: BASF Aktiengesellschaft, Ludwigshafen, Fed. Rep. of Germany

[21] Appl. No.: 971,270

[22] Filed: Nov. 4, 1992

Related U.S. Application Data

[63] Continuation of Ser. No. 772,343, Oct. 7, 1991, abandoned.

[30] Foreign Application Priority Data

Nov. 30, 1990 [DE] Fed. Rep. of Germany ....... 4038200

[51] Int. Cl.$^5$ ............................................. C07C 317/36
[52] U.S. Cl. ..................................... 564/218; 534/640;
534/642; 558/413; 560/10; 560/12; 562/58;
562/68; 562/427; 562/430; 564/222; 564/308;
564/309; 564/315; 564/323; 564/374; 564/378;
564/428
[58] Field of Search ............... 534/640, 642; 564/440,
564/218, 222, 308, 309, 319, 323, 374, 378, 428;
558/413; 560/10, 12; 562/427, 430, 58, 68

[56] References Cited

U.S. PATENT DOCUMENTS

| 2,938,042 | 5/1960 | Stevenson et al. | 564/440 X |
| 3,804,904 | 4/1974 | Bentley et al. | 364/440 X |

FOREIGN PATENT DOCUMENTS

| 1302434 | 7/1962 | France | 534/642 |
| 1562354 | 4/1969 | France | 534/642 |
| 928492 | 6/1963 | United Kingdom | 534/640 |

OTHER PUBLICATIONS

Houben-Weyl, "Methoden der Organischem Chemie," 1977, vol. V/2a, pp. 975 and 1074.

Primary Examiner—Richard L. Raymond
Attorney, Agent, or Firm—Oblon, Spivak, McClelland, Maier, & Neustadt

[57] ABSTRACT

Sulfonyl compounds of the formula

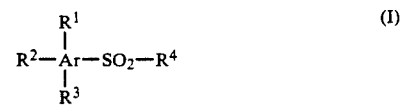

where
 Ar is the radical of a benzene or naphthalene ring,
 $R^1$ and $R^2$ are each hydrogen, substituted or unsubstituted $C_1$-$C_4$-alkyl, substituted or unsubstituted phenyl, $C_1$-$C_4$-alkoxy, carboxyl, $C_1$-$C_4$-alkoxycarbonyl, cyano, halogen or hydroxysulfonyl,
 $R^3$ is nitro, amino, $C_1$-$C_4$-alkanoylamino or benzoylamino, and
 $R^4$ is a radical of the formula

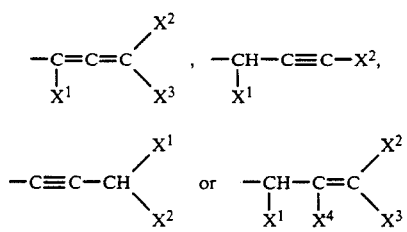

where
 $X^1$, $X^2$ and $X^3$ are each hydrogen, substituted or unsubstituted $C_1$-$C_4$-alkyl or substituted or unsubstituted phenyl, and
 $X^4$ is a group which is detachable under alkaline conditions, either in the free form or in the form of their salts, are useful for synthesizing reactive dyes.

2 Claims, No Drawings

ARYLSULFONYL COMPOUNDS WITH UNSATURATED RADICALS

This application is a continuation of application Ser. No. 07/772,343, filed on Oct. 7, 1991, now abandoned.

The present invention relates to novel sulfonyl compounds of the formula I

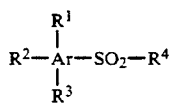

where
Ar is the radical of a benzene or naphthalene ring,
$R^1$ and $R^2$ are identical or different and each is independently of the other hydrogen, unsubstituted or amino- or $C_1$–$C_4$-alkanoylamino-substituted $C_1$–$C_4$-alkyl, substituted or unsubstituted phenyl, $C_1$–$C_4$-alkoxy, carboxyl, $C_1$–$C_4$-alkoxycarbonyl, cyano, halogen or hydroxysulfonyl,
$R^3$ is nitro, amino, $C_1$–$C_4$-alkanoylamino or benzoylamino, and
$R^4$ is a radical of the formula

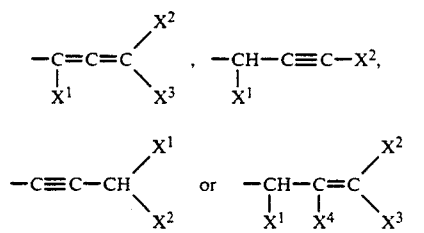

where
$X^1$, $X^2$ and $X^3$ are identical or different and each is independently of the others hydrogen, unsubstituted or hydroxyl- or $C_1$–$C_4$-alkoxy-substituted $C_1$–$C_4$-alkyl or substituted or unsubstituted phenyl, and
$X^4$ is a group which is detachable under alkaline reaction conditions,
in the free form or in the form of a salt thereof, the preparation thereof and the use of those sulfonyl compounds where $R^3$ is amino for the synthesis of reactive dyes.

It is an object of the present invention to provide novel arylsulfonyl compounds which have unsaturated radicals and which shall be advantageous for use as reactive systems for reactive dyes and, if they additionally contain an amino group, also as diazo components. It is a further object to provide a suitable process for preparing the novel compounds in an advantageous manner.

We have found that these objects are achieved by the above-defined sulfonyl compounds of the formula I.

Any alkyl appearing in the abovementioned formula I may be either straight-chain or branched.

Any substituted phenyl appearing in the abovementioned formula I may have as substituents for example $C_1$–$C_4$-alkyl, $C_1$–$C_4$-alkoxy or halogen. The phenyl will ordinarily have from 1 to 3 substituents.

$R^1$, $R^2$, $X^1$, $X^2$ and $X^3$ are each for example methyl, ethyl, propyl, isopropyl, butyl, isobutyl, sec-butyl, phenyl, 2- or 4-methylphenyl, 2,4-dimethylphenyl, 2- or 4-chlorophenyl, 2,4-dichlorophenyl, 2- or 4-methoxyphenyl or 2,4-dimethoxyphenyl.

$R^1$ and $R^2$ may each also be for example fluorine, chlorine, bromine, methoxy, ethoxy, propoxy, isopropoxy, butoxy, isobutoxy, sec-butoxy, aminomethyl, 2-aminoethyl, 2- or 3-aminopropyl, 2- or 4-aminobutyl, formylaminomethyl, acetylaminomethyl, propionylaminomethyl, 2-formylaminoethyl, 2-acetylaminoethyl, 2-propionylaminoethyl, 2-or 3-propionylaminopropyl, 2- or 4-formylaminobutyl, 2- or 4-acetylaminobutyl, 2- or 4-propionylaminobutyl, methoxycarbonyl, ethoxycarbonyl, propoxycarbonyl, isopropoxycarbonyl or butoxycarbonyl.

$R^3$ may also be for example formylamino, acetylamino, propionylamino, butyrylamino or isobutyrylamino.

$X^1$, $X^2$ and $X^3$ may each also be for example hydroxymethyl, 2-hydroxyethyl, 2- or 3-hydroxypropyl, 2- 4-hydroxybutyl, methoxymethyl, ethoxymethyl, 2-methoxyethyl, 2-ethoxyethyl, 2- or 3-methoxypropyl, 2- or 3-ethoxypropyl, 2- or 4-methoxybutyl or 2- or 4-ethoxybutyl.

$X^4$ in the formula I is a group which is detachable under alkaline conditions. Such groups are for example halogen, such as chlorine, bromine or iodine, $OSO_3H$, $SSO_3H$, $OP(O)(OH)_2$, $C_1$–$C_4$-alkylsulfonyloxy, substituted or unsubstituted phenylsulfonyloxy, $C_1$–$C_4$-alkanoyloxy, $C_1$–$C_4$-dialkylamino or a radical of the formula

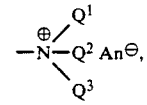

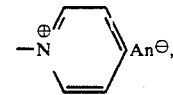

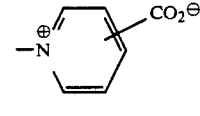

or

where $Q^1$, $Q^2$ and $Q^3$ are identical or different and each is independently of the others $C_1$–$C_4$-alkyl or benzyl and An$\ominus$ is in each case an anion. Suitable anions A$\ominus$ are for example fluoride, chloride, bromide, iodide, mono-, di- or trichloroacetate, methanesulfonate, benzenesulfonate and 2- or 4-methylbenzenesulfonate. Preferably, $X^4$ is halogen.

The sulfonyl compounds of the formula I can be present either in the free form or in the form of their salts. If they have hydroxysulfonyl or carboxyl groups, they can be for example in the form of the alkali metal salts, for example the lithium, sodium or potassium salts, or in the form of ammonium salts.

If they have amino groups, they can be for example in the form of the halides, such as fluoride, chloride, bromide or iodide, or in the form of bisulfate or sulfate.

If they have both hydroxylsulfonyl or carboxyl and amino groups, they can also be in the betaine form.

Of particular note are sulfonyl compounds of the formula I where one of $R^1$ and $R^2$ is hydrogen and the other is likewise hydrogen or unsubstituted or amino- or $C_1$-$C_4$-alkanoylamino-substituted $C_1$-$C_4$-alkyl, $C_1$-$C_4$-alkoxy or halogen.

Preference is given to sulfonyl compounds of the formula I where $R^4$ is a radical of the formula

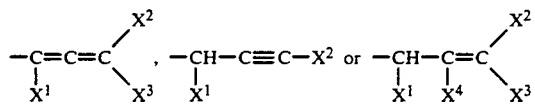

where $X^1$, $X^2$ and $X^3$ are each hydrogen, and $X^4$ is halogen.

Particular preference is given to sulfonyl compounds of the formula I where $R^4$ is a radical of the formula

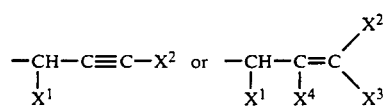

where $X^1$, $X^2$ and $X^3$ are each hydrogen, and $X^4$ is halogen.

As indicated earlier, we have also found an advantageous process for preparing sulfonyl compounds of the formula Ia

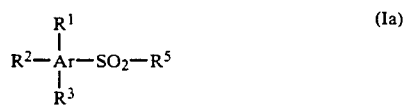

where Ar, $R^1$, $R^2$ and $R^3$ are each as defined above and $R^5$ is a radical of the formula

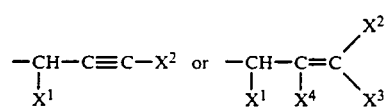

where $X^1$, $X^2$, $X^3$ and $X^4$ are each as defined above, by reacting arylsulfinic acids of the formula II

with halogen compounds of the formula IIIa or IIIb

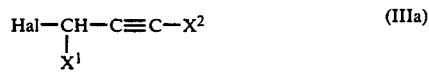

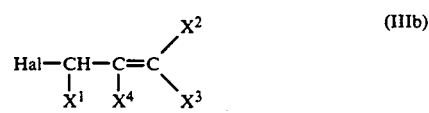

where Hal is in each case halogen and Ar, $R^1$, $R^2$, $R^3$, $X^1$, $X^2$, $X^3$ and $X^4$ are each as defined above, in an aqueous medium at from 20° to 95° C. by carrying out the reaction at a pH of from 2.5 to 7, preferably from 4 to 6.5.

The process of the present invention is in general carried out in water or in a mixture of water and a water-miscible solvent. Suitable water-miscible solvents are for example $C_1$-$C_4$-alkanols, such as methanol, ethanol, propanol, isopropanol, butanol or isobutanol, N,N-dimethylformamide, N-methylpyrrolidinone, tetrahydrofuran and acetone.

Advantageously, the reactants are brought together by adding the halogen compound IIIa or IIIb to the initial charge of arylsulfinic acid II in water or in a mixture of water and a water-miscible solvent.

The pH is in general set with a base, for example sodium carbonate or potassium carbonate, since the arylsulfinic acids give a strongly acidic reaction.

The advantage of the novel process is that, compared with existing processes, which are carried out in a basic medium, the formation of by-products is suppressed when working in an acidic medium.

The sulfonyl compounds of the formula Ia obtained in the process of the present invention can then be used to obtain those sulfonyl compounds in which $R^4$ is a radical of the formula

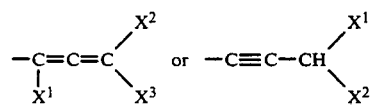

where $X^1$, $X^2$ and $X^3$ are each as defined above, for example by treatment with a base (see for example Houben-Weyl, "Methoden der Organischen Chemie", volume V/2a, pages 975 and 1074).

The novel sulfonyl compounds of the formula I are useful intermediates for the synthesis of dyes.

More particularly, those sulfonyl compounds of the formula Ib

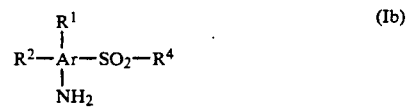

where $R^1$, $R^2$ and $R^4$ are each as defined above, are useful as reactive system and possibly also as diazo component in the preparation of reactive dyes.

The Examples which follow will further illustrate the invention.

EXAMPLE 1

A solution of 398 g of p-acetylaminobenzenesulfinic acid in 1000 ml of water was adjusted to pH 7 with sodium carbonate. This solution was added dropwise to a 60° C. mixture of 444 g of 2,3-dichloroprop-1-ene, 500 ml of tetrahydrofuran (THF) and 500 ml of water over 8 hours. The reaction mixture was subsequently stirred at 60° C. for a further 4 hours. Throughout the entire reaction time the pH was maintained at from 6.5 to 6.9 by the dropwise addition of 5 % strength by weight sodium bicarbonate solution. After cooling, insolubles were filtered off, and the filtrate was saturated with sodium chloride and repeatedly extracted with ethyl acetate. The solvent was evaporated off under reduced pressure to leave 163.5 g of the compound of the formula

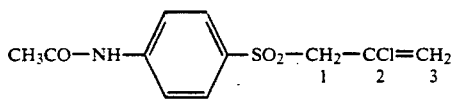

¹H-NMR (D₆-DMSO): δ=2.1 (s, 3H, CH₃), 4.5 (s, 2H, 1-H), 5.4 (s, 1H, 3-H), 5.6 (s, 1H, 3-H), 7.8 (brs, 4H, aromatic H), 10.4 (s, 1H, NH) ppm.

EXAMPLE 2

40 g of the compound of Example 1 were heated in 500 g of half-concentrated hydrochloric acid at 60° C. for 7 hours. The reaction solution was then concentrated under reduced pressure at 50° C. 39 g were isolated of the compound of the formula

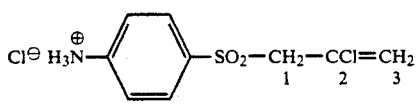

¹H-NMR (D₆-DMSO): δ=4.3 (s, 2H, 1-H), 5.4 (s, 1H, 3-H), 5.5 (s, 1H, 3-H), 6.9 (d, 2H, aromatic H), 7.6 (d, 2H, aromatic H), 8.3 (brs, 3H, NH₃⊕) ppm.

EXAMPLE 3

A solution of 199 g of p-acetylaminobenzenesulfinic acid in 500 ml of water was adjusted to pH 7 with sodium carbonate. This solution was added dropwise to a 40°–45° C. mixture of 219.8 g of 2,3-dibromoprop-1-ene, 250 ml of THF and 250 ml of water over 1 hour. The reaction mixture was subsequently stirred at 40°–45° C. for a further 3 hours. Throughout the entire reaction time the pH was maintained at from 6.5 to 6.9 by the dropwise addition of 5 % strength by weight sodium bicarbonate solution. After cooling, the mixture was worked up as in Example 1 to isolate 207 g of compound of the formula

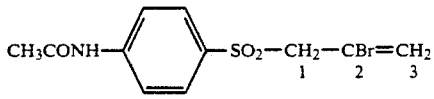

¹H-NMR (D₆-DMSO): δ=2.1 (s, 3H, CH₃), 4.5 (s, 2H, 1-H), 5.7 (s, 1H, 3-H), 5.9 (s, 1H, 3-H), 7.9 (brs, 4H, aromatic H), 10.3 (brs, 1H, NH) ppm.

EXAMPLE 4

32 g of the compound of Example 3 were hydrolyzed in 300 g of half-concentrated hydrochloric acid as described in Example 2. 31 g were isolated of a substance which according to NMR spectroscopy has the following structure:

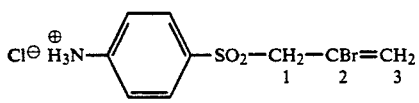

¹-NMR (D₆-DMSO): δ=4.4 (s, 2H, 1-H), 5.7 (s, 1H, 3-H), 5.8 (s, 1H, 3-H), 6.85 (d, 2H, aromatic H), 7.6 (d, 2H, aromatic H), 8.3 (brs, 3H, NH₃⊕) ppm.

The procedures of Examples 1 and 2 are repeated to obtain the compounds of the formula

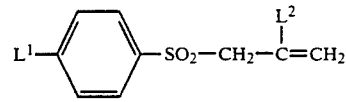

listed below in Table 1.

TABLE 1

| Example No. | L¹ | L² |
|---|---|---|
| 5 | CH₃CO—NHCH₂CH₂ | Cl |
| 6 | Cl⊖H₃N⊕CH₂CH₂ | Cl |
| 7 | CH₃CO—NHCH₂CH₂ | Br |
| 8 | Cl⊖H₃N⊕CH₂CH₂ | Br |

EXAMPLE 9

187 g of m-nitrobenzenesulfinic acid were dissolved in 1 l of water at pH 7 and added dropwise to an 80° C. mixture of 222 g of 2,3-dichloroprop-1-ene in 200 ml of water over 4 hours. The mixture was subsequently stirred at 80° C. for 8 hours, during which the pH was allowed to fall to about 2.5. After cooling, the precipitate was filtered off with suction and dried under reduced pressure at 50° C. 209 g were isolated of the compound of the formula

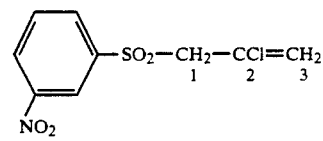

¹H-NMR (D₆-DMSO): δ=4.8 (s, 2H, 1-H), 5.5 (s, 1H, 3-H), s, 1H, 3-H), 8.0 (t, 1H, aromatic H), 8.4 (d, 1H, aromatic H), 8.7 (m, 2H, aromatic H) ppm.

EXAMPLE 10

26.2 g of the compound of Example 9 were dissolved in 300 g of methanol and 2 g of propionic acid. 5 g of Raney nickel were added for a hydrogenation at 40° C. under a hydrogen pressure of 2 bar. When hydrogen absorption was complete, the catalyst was filtered off and the mother liquor was freed of solvent. This left 22.5 g of the compound of the formula

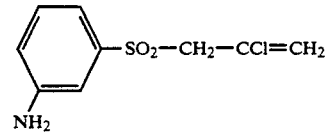

which can be used for dye syntheses without further purification.

The procedures of Examples 9 and 10 are repeated to obtain the compounds of the formula

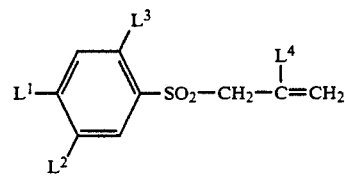

listed below in Table 2.

TABLE 2

| Example No. | L¹ | L² | L³ | L⁴ |
|---|---|---|---|---|
| 11 | H | NO₂ | H | Br |
| 12 | H | NH₂ | H | Br |
| 13 | H | NO₂ | Cl | Cl |
| 14 | H | NH₂ | Cl | Cl |
| 15 | H | NO₂ | Cl | Br |
| 16 | H | NH₂ | Cl | Br |
| 17 | Cl | NO₂ | H | Cl |
| 18 | Cl | NH₂ | H | Cl |
| 19 | Cl | NO₂ | H | Br |
| 20 | Cl | NH₂ | H | Br |
| 21 | H | NH₂ | CH₃ | Cl |
| 22 | H | NH₂ | CH₃ | Br |
| 23 | H | NH₂ | N(CH₃)₂ | Cl |
| 24 | H | NH₂ | N(CH₃)₂ | Br |
| 25 | H | NH₂ | NHCH₂CH₂OH | Cl |
| 26 | H | NH₂ | NHCH₂CH₂OH | Cl |
| 27 | H | NH₂ | OCH₃ | Cl |

EXAMPLE 28

160 g (0.64 mol) of 2-acetylaminonaphthalene-6-sulfinic acid were dissolved in 1000 ml of water at pH 6, and the solution was added to a solution of 78.5 g (0.71 mol) of 2,3-dichloroprop-1-ene and 80 ml of THF. The reaction mixture was heated at about 70° C. for about 10 hours. After the reaction had ended (check by TLC), the precipitate which had formed was filtered off with suction at about 10° C., washed with water and dried, leaving 163.3 g of a compound of the formula

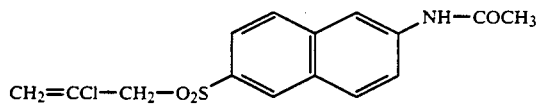

having a melting point of from 148° to 152° C.

¹H-NMR (D₆-DMSO): δ=2.16 (s, 3H, CH:), 3.35 (t, 1H, C≡CH), 4.60 (d, 2H, CH₂), 7.80–8.55 (m, 6H, aromatic H), 10.33 (s, 1H, NH) ppm.

EXAMPLE 29

160 g (0.5 mol) of the compound described in Example 28 were heated to the boil together with 740 g of 10 % strength by weight hydrochloric acid. After the deacetylation had ended (check by TLC), the reaction mixture was cooled down to about 10° C. and the precipitate was filtered off with suction, 146 g having been produced of a compound of the formula

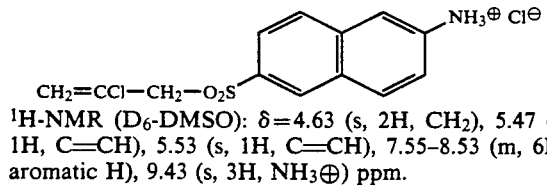

¹H-NMR (D₆-DMSO): δ=4.63 (s, 2H, CH₂), 5.47 (s, 1H, C═CH), 5.53 (s, 1H, C═CH), 7.55–8.53 (m, 6H, aromatic H), 9.43 (s, 3H, NH₃⊕) ppm.

EXAMPLE 30

160 g (0.64 mol) of 2-acetylaminonaphthalene-6-sulfinic acid were dissolved in 1000 ml of water at pH 6 and the solution was added dropwise to a solution of 84.1 g (0.7 mol) of 3-bromoprop-1-yne and 85 ml of THF. After the addition was complete, the reaction mixture was heated at from 40° to 60° C. until the reaction had ended (check by TLC). The precipitate formed was filtered off with suction at about 10° C., washed with water and dried, leaving 166.4 g of 2-acetylamino-6-(prop-1-yn-3-ylsulfonyl)naphthalene of the formula

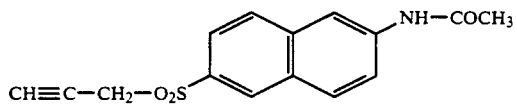

having a melting point of from 230° to 238° C.

¹H-NMR (D₆-DMSO): δ=2.16 (s, 3H, CH₃), 3.35 (t, 1H, C≡CH), 4.6 (d, 2H, CH:), 7.8–8.55 (m, 6H, aromatic H), 10.33 (s, 1H, NH) ppm.

EXAMPLE 31

59 g (0.26 mol) of 2-acetylamino-6-(prop-1-yn-3-ylsulfonyl)naphthalene were heated at 100° C. in 400 ml of 10 % strength by weight hydrochloric acid for 2 hours. The hot solution was clarified, and the precipitate, which formed on cooling, was filtered off with suction at about 10° C., washed and dried. This left 54 g of 2-amino-6-(prop-1-yn-3-ylsulfonyl)naphthalene hydrochloride (melting point 208°–213° C).

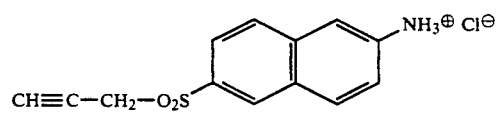

¹H-NMR (D₆-DMSO): δ=3.5 (1H, C≡C), 4.73 (2H, CH₂), 7.7–8.7 (6H, aromatic H), 8.85 (3H, NH₃⊕) ppm.
¹³C-NMR (D₆-DMSO): δ=7.1 (CH₂), 72.8 (C≡C), 78.1 (C≡CH), 118.6, 122.8, 124.0, 128.6, 129.3, 129.9, 131.3, 134.4, 135.2, 135.8 (aromatic C) ppm.

EXAMPLE 32

199 g (1.0 mol) of 4-acetylaminobenzenesulfinic acid were dissolved in 1000 ml of water at pH 6, the solution was added dropwise to a solution of 140 g (1.1 mol) of 3-bromoprop-1-yne and 200 ml of THF at from 40° to 50° C., and the mixture was maintained at that temperature until the reaction had ended (check by TLC). The precipitate formed was filtered off with suction at about 10° C., washed neutral with water and dried, leaving 205 g of 4-acetylamino-1-(prop-1-yn-3-ylsulfonyl)benzene (melting point 175°–179° C.).

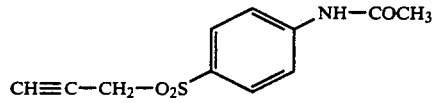

¹H-NMR (D₆-DMSO): δ=2.13 (3H, CH₃), 3.4 (1H, C≡CH), 4.47 (2H, CH₂), 7.83–7.92 (4H, aromatic), 10.45 (1H, NH) ppm. ¹³C-NMR (D₆-DMSO): δ=4.1 (CH:), 47.2 (CH₂), 73.0 (C≡C), 77.8 (C≡CH), 118.4, 129.6, 131.3, 144.4 (aromatic C), 169.1 (C═O) ppm.

EXAMPLE 33

205 g (0.865 mol) of 4-acetylamino-1-(prop-1-yn-3-ylsulfonyl)benzene were heated at the boil in 1000 ml of 10 % strength by weight hydrochloric acid for about 1.5 hours. After deacetylation had ended (check by TLC), the reaction mixture was clarified and cooled down to about 10° C. The precipitate formed was filtered off with suction, washed with a little 10 % strength by weight hydrochloric acid and dried, leaving 168 g of 4-amino-1-(prop-1-yn-3-ylsulfonyl)benzene hydrochloride (melting point 225°–229° C.).

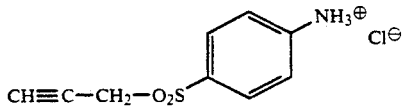

$^1$H-NMR (D$_6$-DMSO): δ=3.37 (t, 1H, C≡CH), 4.33 (d, 2H, CH$_2$), 6.90–7.65 (4H, aromatic H), 8.5 (3H, NH$_3\oplus$) ppm. $^{13}$C-NMR (D$_6$-DMSO): δ=47.6 (CH:), 73.4 (C≡C), 77.3 (C≡CH), 14.4, 125.1, 130.1, 151.4 (aromatic C) ppm.

EXAMPLE 34

110.7 g (0.5 mol) of 2-chloro-5-nitrobenzenesulfinic acid were dissolved in 500 ml of water at pH 6.5 and the solution was added to a solution of 65.5 g (0.55 mol) of 3-bromoprop-1-yne and 100 ml of THF. The reaction mixture was then heated to 40°–50° C. After the reaction had ended (check by TLC), the reaction product was extracted with 1.5 l of ethyl acetate, and the organic phase was neutralized and dried over sodium sulfate. The solvent was evaporated off to leave 95 g of 2-chloro-5-nitro-1-(prop-1-yn-3-ylsulfonyl)benzene (melting point 238°–241° C.).

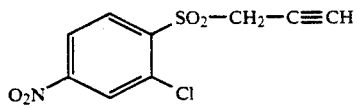

$^1$H-NMR (D$_6$-DMSO): δ=3.43 (t, 1H, C≡CH), 4.82 (d, 2H, CH$_2$), 8.08, 8.62, 8.73 (m, 3H, aromatic H) ppm. $^{13}$C-NMR (D$_6$-DMSO): δ=46.5 (CH:), 71.2 (C TM C), 79.5 (C≡CH), 126.7, 130.1, 133.9, 136.6, 138.4, 146.3 (aromatic C) ppm.

EXAMPLE 35

93.5 g (0.5 mol) of 3-nitrobenzenesulfinic acid were dissolved in 500 ml of water at pH 6.5 and the solution was added to a solution of 65.5 g of 3-bromo-prop-1-yne and 70 ml of THF. The reaction mixture was heated at 40°–50° C. until the reaction had ended (check by TLC). The reaction product was extracted with about 1.5 l of ethyl acetate, and the organic phase was neutralized and dried over sodium sulfate. The solvent was evaporated off to leave 60 g of 3-nitro-1-(prop-1-yn-3-ylsulfonyl)benzene (melting point 250°–255° C.).

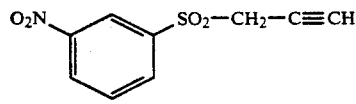

$^1$H-NMR (D$_6$-DMSO): δ=3.42 (t, 1H, C≡CH), 4.72 (d, 2H, CH$_2$), 8.02–8.68 (m, 4H, aromatic H) ppm. $^{13}$C-NMR (D$_6$-DMSO): δ=47.0 (CH:), 72.3 (C≡C), 78.5 (C≡CH), 123.2, 128.8, 131.3, 134.4, 147.9 (aromatic C) ppm.

EXAMPLE 36

99.5 g (0.5 mol) of 3-acetylaminobenzenesulfinic acid were dissolved in 500 ml of water at pH 6.5 and the solution was added dropwise to a mixture of 65.5 g (0.55 mol) of 3-bromoprop-1-yne and 70 ml of THF. To complete the reaction (check by TLC) the reaction mixture was heated to 40°–50° C. The precipitate formed was filtered off with suction at 10° C., washed neutral with water and dried, leaving 83 g of the compound of the formula

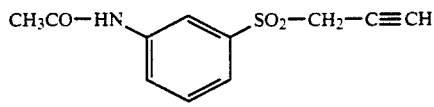

having a melting point of from 159° to 165° C.

$^1$H-NMR (D$_6$-DMSO): δ=2.12 (s, 3H, CH$_3$), 3.43 (t, 1H, C≡CH), 4.53 (d, 2H, CH:), 7.63–8.27 (m, 4H, aromatic H), 10.38 (s, 1H, NH) ppm.

EXAMPLE 37

71.1 g (0.3 mol) of the compound of Example 36 were heated to the boil in 300 ml of 10 % strength by weight hydrochloric acid. After the deacetylation had ended, the reaction mixture was cooled down to 10° C. and the precipitate formed was filtered off with suction, giving 54.2 g of a compound of the formula

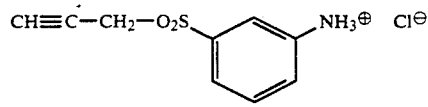

having a melting point of from 213° to 217° C.

$^1$H-NMR (D$_6$-DMSO): δ=3.45 (t, 1H, C≡CH), 4.60 (d, 2H, CH$_2$), 7.55–7.72 (m, 4H, aromatic H), 9.38 (s, 3H, NH$_3\oplus$) ppm.

EXAMPLE 38

119.5 g (0.5 mol) of 3-acetylamino-4-methoxybenzenesulfinic acid were reacted with 65.5 g (0.55 mol) of 3-bromoprop-1-yne as described in Example 30. This produced 97.7 g of a compound of the formula

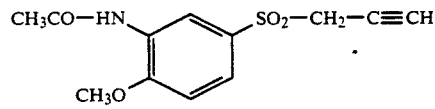

having a melting point of from 140° to 144° C. $^1$H-NMR (D$_6$-DMSO): δ=2.15 (s, 3H, CH$_3$), 3.28 (t, 1H, CH), 3.95 (s, 3H, OCH$_3$), 4.35 (d, 2H, CH$_2$), 7.27–8.63 (m, 3H, aromatic H); 9.28 (s, 1H, NH) ppm.

EXAMPLE 39

79.2 g (0.3 mol) of the compound of Example 38 were deacetylated as described in Example 31. This left 63 g of a solid of the formula

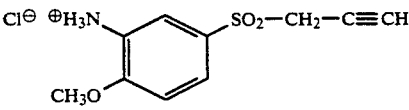

having a melting point of from 209° to 214° C.

$^1$H-NMR (D$_6$-DMSO): δ=3.45 (t, 1H, C≡CH), 3.95 (s, 3H, CH$_3$), 4.47 (d, 2H, CH:), 7.30–7.77 (m, 4H, aromatic H), 9.15 (s, 3H, NH$_3\oplus$) ppm.

EXAMPLE 40

563 g (1.42 mol) of 4-(2-acetylaminoethyl)benzenesulfinic acid were reacted with 190.5 g (1.6 mol) of 3-bromoprop-1-yne as described in Example 30. This produced 307.5 g of the compound

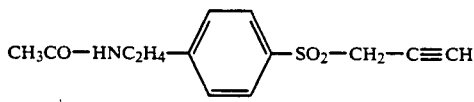

having a melting point of from 117° to 178° C.

$^1$H-NMR (D$_6$-DMSO): δ=1.78 (s, 3H, CH$_3$), 2.87 (t, 2H, CH$_2$), 3.30 (t, 1H, C≡CH), 3.35 (t, 2H, CH$_2$), 4.45 (d, 2H, C≡C—CH$_2$), 7.48, 7.52, 7.87, 7.90 (4H, aromatic H), 7.82 (s, 1H, NH) ppm.

EXAMPLE 41

302 g (1.14 mol) of the compound of Example 40 were heated to the boil together with 1000 ml of 10% strength by weight hydrochloric acid. After the reaction had ended (check by TLC), the reaction mixture was evaporated to dryness, leaving 266 g of a compound of the formula

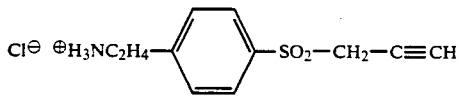

$^1$H-NMR (D$_6$-DMSO): δ=3.13 (2H, CH$_2$), 3.37 (3H, CH$_2$ and C≡CH), 4.47 (2H, C≡C—CH$_2$), 7.60, 7.63, 7.92, 7.95 (4H, aromatic H), 9.32 (3H, NH$_3$) ppm.

Instead of the 3-bromprop-1-yne used in Examples 30, 32, 34, 36, 38 and 40 it is also possible to use 3-chloroprop-1-yne.

Using the same method it is possible to obtain the compounds of the formula

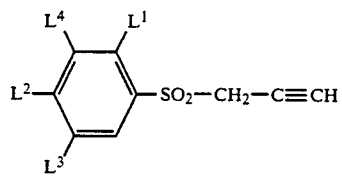

listed below in Table 3.

TABLE 3

| Example No. | L$^1$ | L$^2$ | L$^3$ | L$^4$ |
|---|---|---|---|---|
| 42 | H | CH$_2$—NHCOCH$_3$ | H | H |
| 43 | H | CH$_2$—NH$_2$ | H | H |
| 44 | NHCOCH$_3$ | H | H | H |
| 45 | NH$_2$ | H | H | H |
| 46 | H | CH$_3$ | NHCOCH$_3$ | H |
| 47 | H | CH$_3$ | NH$_2$ | H |
| 48 | H | NHCOCH$_3$ | Cl | H |
| 49 | H | NH$_2$ | Cl | H |
| 50 | H | NHCOCH$_3$ | Cl | CH$_3$ |
| 51 | H | NH$_2$ | Cl | CH$_3$ |
| 52 | H | CH$_3$ | NHCOCH$_3$ | Cl |
| 53 | H | CH$_3$ | NH$_2$ | Cl |
| 54 | Cl | NHCOCH$_3$ | Cl | H |
| 55 | Cl | NH$_2$ | Cl | H |
| 56 | NHCOCH$_3$ | H | Cl | Cl |
| 57 | NH$_2$ | H | Cl | Cl |
| 58 | NHCOCH$_3$ | H | CH$_3$ | CH$_3$ |

TABLE 3-continued

| Example No. | L$^1$ | L$^2$ | L$^3$ | L$^4$ |
|---|---|---|---|---|
| 59 | NH$_2$ | H | CH$_3$ | CH$_3$ |

Using the procedure of Examples 1 and 2 it is possible to obtain further compounds of the formula

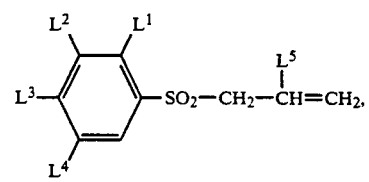

as listed below in Table 4.

TABLE 4

| Example No. | L$^1$ | L$^2$ | L$^3$ | L$^4$ | L$^5$ |
|---|---|---|---|---|---|
| 60 | H | CH$_2$—NHCOCH$_3$ | H | H | Cl |
| 61 | H | CH$_2$—NH$_2$ | H | H | Cl |
| 62 | NHCOCH$_3$ | H | H | H | Cl |
| 63 | NH$_2$ | H | H | H | Cl |
| 64 | H | CH$_3$ | NHCOCH$_3$ | H | Cl |
| 65 | H | CH$_3$ | NH$_2$ | H | Cl |
| 66 | H | NHCOCH$_3$ | Cl | H | Cl |
| 67 | H | NH$_2$ | Cl | H | Cl |
| 68 | H | NHCOCH$_3$ | Cl | CH$_3$ | Cl |
| 69 | H | NH$_2$ | Cl | CH$_3$ | Cl |
| 70 | H | CH$_3$ | NHCOCH$_3$ | Cl | Cl |
| 71 | H | CH$_3$ | NH$_2$ | Cl | Cl |
| 72 | Cl | NHCOCH$_3$ | Cl | H | Cl |
| 73 | Cl | NH$_2$ | Cl | H | Cl |
| 74 | NHCOCH$_3$ | H | Cl | Cl | Cl |
| 75 | NH$_2$ | H | Cl | Cl | Cl |
| 76 | NHCOCH$_3$ | H | CH$_3$ | CH$_3$ | Cl |
| 77 | NH$_2$ | H | CH$_3$ | CH$_3$ | Cl |

Instead of the 2,3-dichloroprop-1-ene used in Examples 1 and 2 and 60 to 77 it is also possible to use 2,3-dibromoprop-1-ene, in which case the corresponding

EXAMPLE 78

24 g (0.1 mol) of 4-acetylamino-1-(prop-1-yn-3-ylsulfonyl)benzene (Example 32) were dissolved in 100 ml of THF, admixed with 1 g (0.01 mol) of triethylamine and heated to the boil. After the isomerization had ended (check by TLC), the solvent was evaporated off and the residue was recrystallized from ethyl acetate. This left 20 g of a compound of the formula

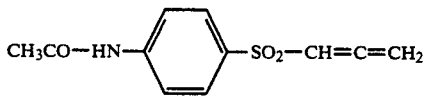

$^1$H-NMR (D$_6$-DMSO): δ=2.12 (s, 3H, CH$_3$), 5.68 (d, 2H, CH$_2$), 6.70 (t, 1H, CH), 7.80–7.88 (m, 4H, aromatic H), 10.33 (s, 1H, NH) ppm.

EXAMPLE 79

26.7 g (0.1 mol) of 3-acetylamino-4-methoxy-1-(prop-1-yn-3-ylsulfonyl)benzene (Example 38) were reacted with 0.01 mol of triethylamine as described in Example 78. This produced 24 g of a compound of the formula

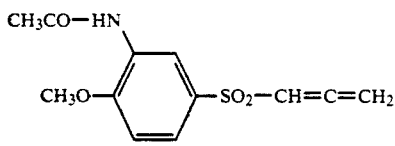

$^1$H-NMR (D$_6$-DMSO): δ=2.15 (s, 3H, CH$_3$), 3.97 (s, 3H, OCH$_3$), 5.68 (d, 2H, CH:), 6.85 (t, 1H, CH), 7.25, 7.57, 8.58 (3H, aromatic H), 9.32 (s, 1H, NH) ppm.

EXAMPLE 80

27.4 g (0.1 mol) of 4-acetylamino-1-(2-chloroprop-1-en-3-ylsulfonyl)benzene (Example 1) were dissolved in 150 ml of THF, admixed with 10.1 g (0.1 mol) of triethylamine and heated to the boil. After the reaction had ended (check by TLC), the precipitate was filtered off with suction, the filtrate was concentrated, and the residue was recrystallized with ethyl acetate. This left 19 g of 4-acetylamino-1-(propa-1,2-dien-3-ylsulfonyl)-benzene, which is identical to the compound described in Example 78.

Using the procedures of Examples 78 and 80 it is possible to obtain the compounds of the formula

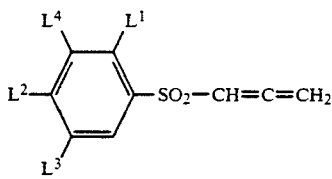

listed below in Table 5.

TABLE 5

| Example No. | L$^1$ | L$^2$ | L$^3$ | L$^4$ |
|---|---|---|---|---|
| 81 | H | CH$_2$—NHCOCH$_3$ | H | H |
| 82 | NHCOCH$_3$ | H | H | H |
| 83 | H | CH$_3$ | NHCOCH$_3$ | H |
| 84 | H | NHCOCH$_3$ | Cl | H |
| 85 | H | NHCOCH$_3$ | Cl | CH$_3$ |
| 86 | H | CH$_3$ | NHCOCH$_3$ | Cl |
| 87 | CL | NHCOCH$_3$ | Cl | H |
| 88 | NHCOCH$_3$ | H | Cl | Cl |
| 89 | NHCOCH$_3$ | H | CH$_3$ | CH$_3$ |
| 90 | H | CH$_3$CONH—CH$_2$CH$_2$ | H | H |
| 91 | H | H | NO$_2$ | H |
| 92 | Cl | NO$_2$ | H | H |

The acetylamino compounds listed can be converted into the corresponding amino compounds as described in Examples 2, 29 and 31.

We claim

1. A sulfonyl compound of the formula I

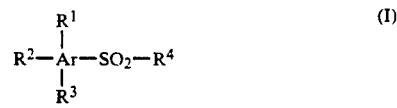

where
Ar is the radical of a benzene or naphthalene ring,
R$^1$ and R$^2$ are identical or different and each is independently of the other hydrogen, unsubstituted or amino- or C$_1$–C$_4$-alkanoylamino-substituted C$_1$–C$_4$-alkyl, substituted or unsubstituted phenyl, C$_1$–C$_4$-alkoxy, carboxyl, C$_1$–C$_4$-alkoxycarbonyl, cyano, halogen or hydroxysulfonyl,
R$^3$ is amino and
R$^4$ is a radical of the formula

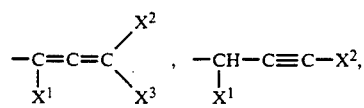

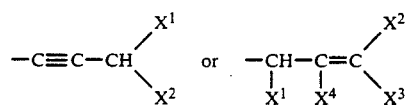

where
X$^1$, X$^2$ and X$^3$ are identical or different and each is independently of the others hydrogen, unsubstituted or hydroxyl- or C$_1$–C$_4$-alkoxy-substituted C$_1$–C$_4$-alkyl or substituted or unsubstituted phenyl, and
X$^4$ is a group which is detachable under alkaline reaction conditions,
in the free form or in the form of a salt thereof.

2. A sulfonyl compound as claimed in claim 1, wherein R$^4$ is a radical of the formula

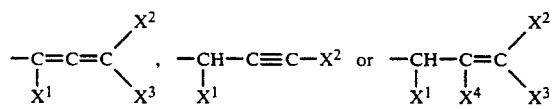

where X$^1$, X$^2$ and X$^3$ are each hydrogen, and X$^4$ is halogen.

* * * * *